United States Patent [19]

Dove et al.

[11] Patent Number: 5,006,472

[45] Date of Patent: Apr. 9, 1991

[54] ENZYMATIC PURIFICATION PROCESS

[75] Inventors: George B. Dove, Hercules; Gautam Mitra, Kensington, both of Calif.

[73] Assignee: Miles Inc., Elkhart, Ind.

[21] Appl. No.: 202,726

[22] Filed: Jun. 3, 1988

[51] Int. Cl.$^5$ ............................................. C12N 1/08
[52] U.S. Cl. ...................... 435/270; 435/262; 435/267; 435/268; 435/272
[58] Field of Search .............. 435/270, 272, 262; 436/548

[56] References Cited

U.S. PATENT DOCUMENTS

| | | | |
|---|---|---|---|
| 3,496,065 | 2/1970 | Russell | 435/270 |
| 3,867,255 | 2/1975 | Newell et al. | 435/270 |
| 3,887,431 | 6/1975 | Robbins et al. | 435/270 X |
| 4,361,587 | 11/1982 | Brule et al. | 435/272 |
| 4,729,958 | 3/1988 | Drozd et al. | 435/270 |

Primary Examiner—Sam Rosen
Attorney, Agent, or Firm—James A. Giblin

[57] ABSTRACT

Controlled enzymatic treatment may be used to selectively degrade undesirable contaminants to a size or charge range which can be more readily removed by subsequent separation steps. Treatment is especially useful for purifying rDNA or monoclonal antibody culture products by using nuclease enzyme treatment to degrade undesirable residual nucleic acids to a molecular size or charge range sufficiently different from the product to be purified so that this difference can be exploited in a subsequent purification step (e.g. precipitation, size exclusion chromatography or ion exchange chromatography). The nuclease enzyme treatment is done in the presence of a detergent.

11 Claims, 2 Drawing Sheets

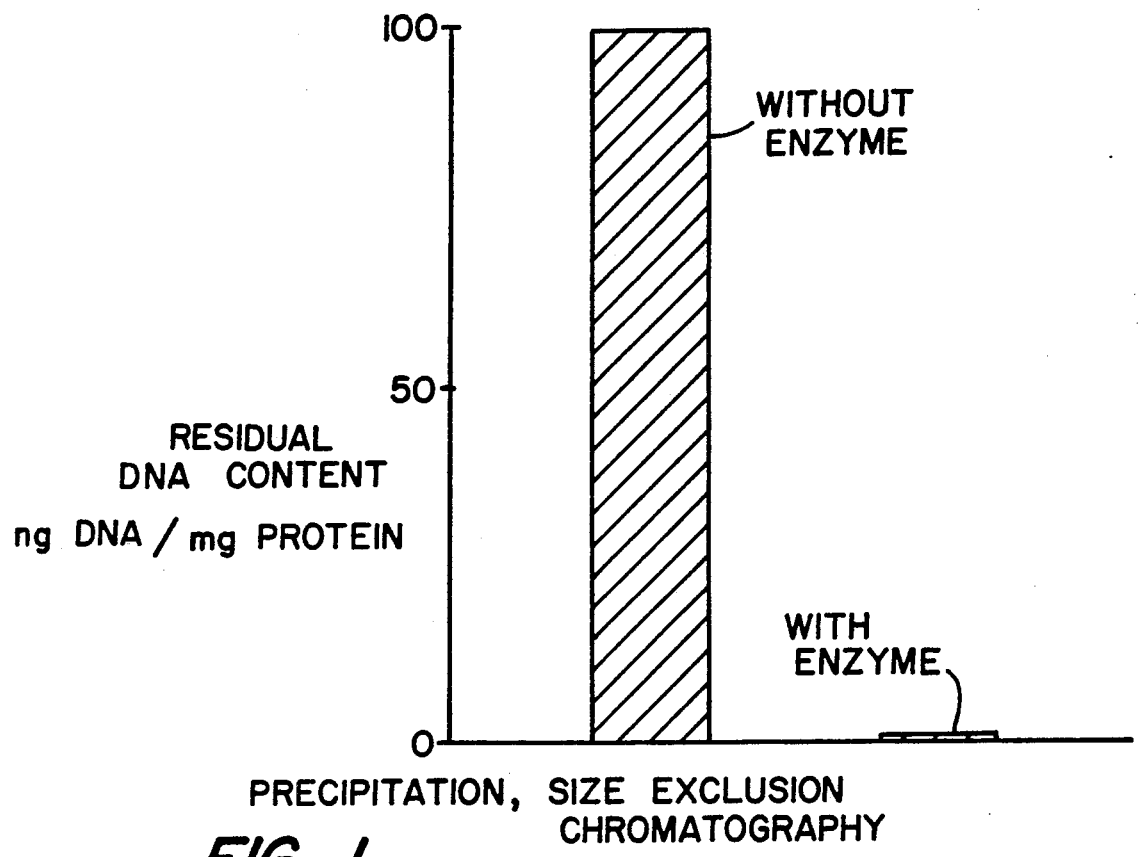
FIG._1.
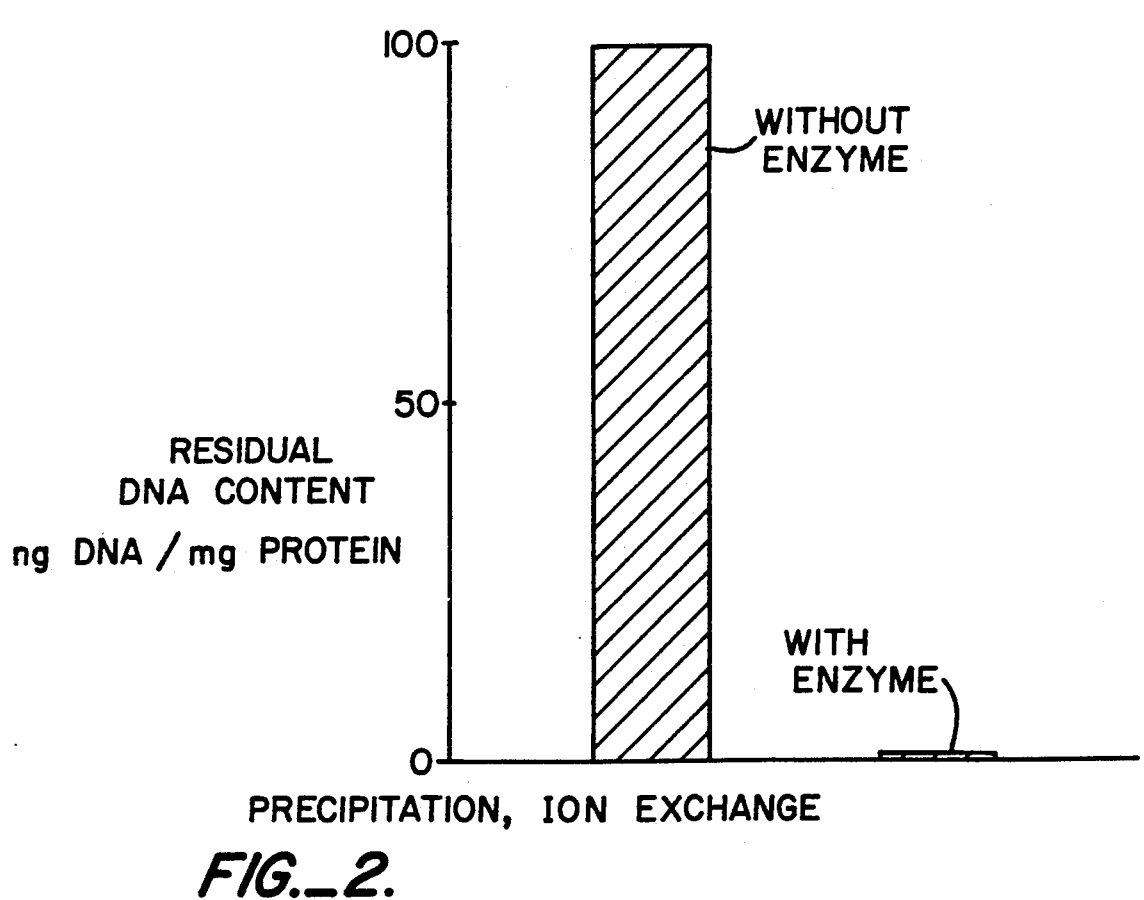
FIG._2.

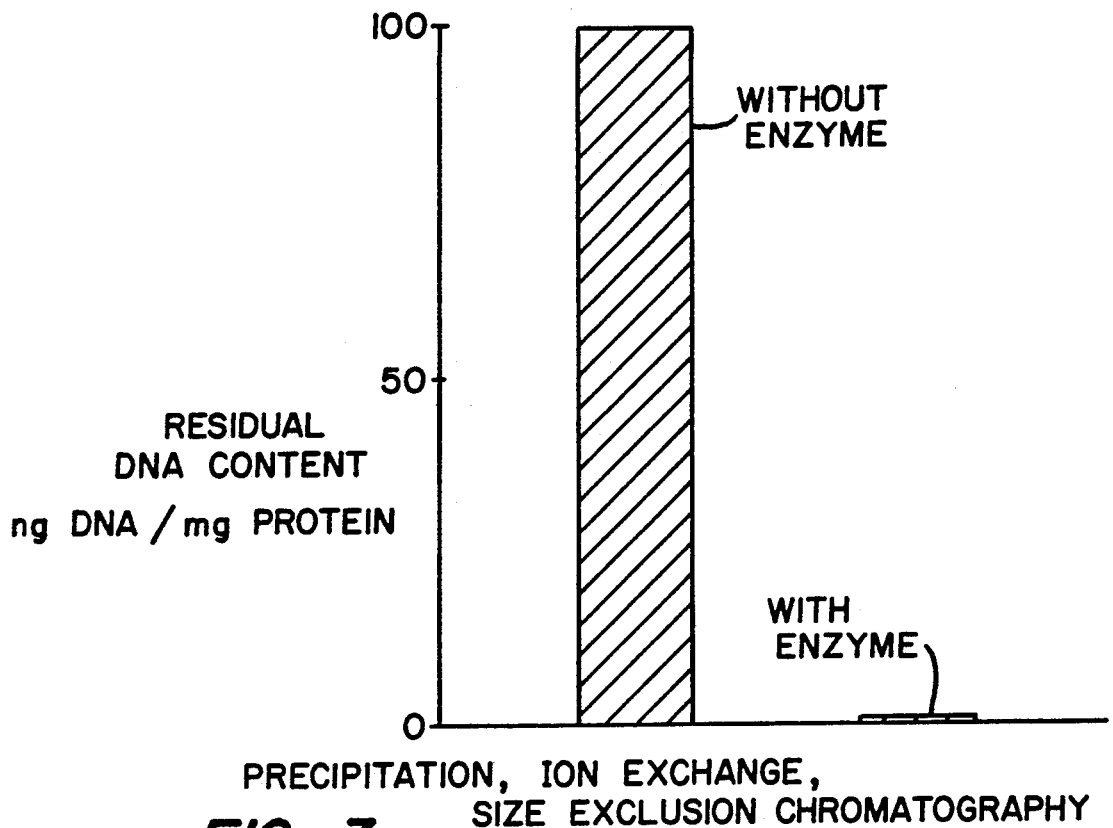
FIG._3.
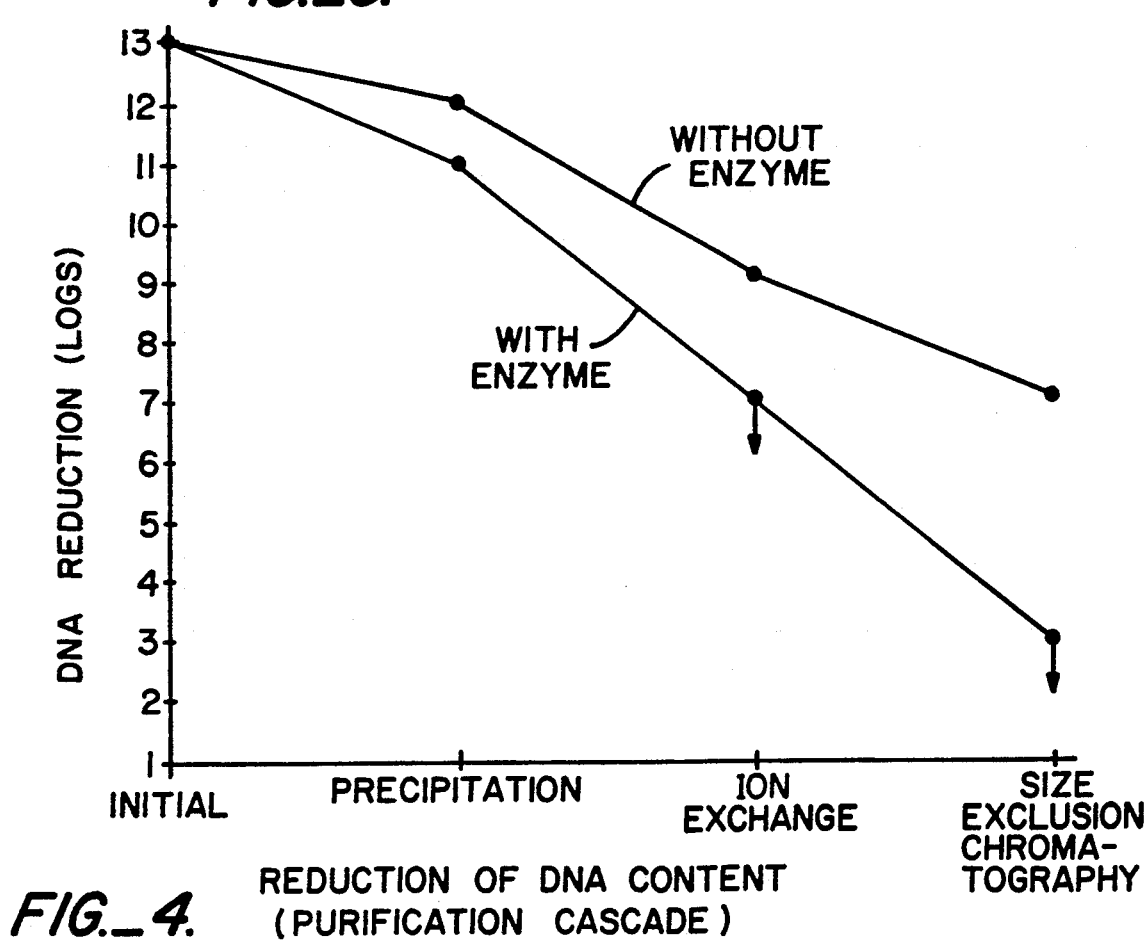
FIG._4.

ENZYMATIC PURIFICATION PROCESS

BACKGROUND OF THE INVENTION

1. Field

This disclosure is concerned generally with the purification of products in biological fluids and specifically with the use of enzymes to selectively degrade unwanted substances to a size range that facilitates the removal of the undesirable substances.

2. Prior Art

Enzymes are relatively complex proteinaceous substances produced by living cells and capable of accelerating very specific chemical reactions. Sometimes referred to as biological catalysts, enzymes have long been used in a variety of industrial, medical and laboratory applications. For example, proteolytic enzymes have been used in laundry detergents to help remove proteinaceous stains, thrombolytic enzymes have been used to dissolve blood clots and hydrolytic enzymes have been used as chromogenic labels useful for immunoassays. Enzymes have been used for a variety of applications in solution (free) and in a so-called immobilized form where they are entrapped or attached via ionic or covalent bonds to supporting materials known as carriers or matrices.

It is well known that enzyme use can be optimized by controlling the conditions of their use (e.g. enzymes typically have an optimal pH range). It is also well known that very specific enzymes such as DNA-ASES are available commercially, especially for use in emerging biotechnology applications where such enzymes are used to accurately cut a nucleic acid at a precise point. To date, however, we are unaware of the use of such enzymes in a controlled manner to facilitate a purification process, especially the purification of therapeutic substances expressed in a cell culture. Surprisingly, we have now found that enzymes can now be used in a relatively simple method to facilitate the purification of various substances, especially biologically active substances generated in various cell cultures where nucleic acids may be present as contaminants. Details of our methods are described below.

SUMMARY OF THE INVENTION

We have found that it is possible to facilitate the removal of an undesirable substance from a cell culture fluid by using a controlled enzymatic incubation to degrade the undesirable substance to a size or charge range that is sufficiently different from the size or charge range of a desirable therapeutic substance to be purified. This enzymatically effected size reduction can then be exploited to facilitate an enhanced separation using techniques that are, to some extent at least, based on differences in molecular size or charge (e.g. size exclusion chromatography, precipitation steps, use of membranes or fibers of controlled pore sizes, etc.). In one preferred embodiment, enzymes known as nucleases (DNA-ases or RNA-ases) are incubated with a cell culture fluid containing both undesirable nucleic acids (RNAs or DNAs) and a desirable substance expressed into the cell culture fluid (e.g. a monoclonal antibody or a biologically active protein expressed using recombinant DNA technologies). The incubation is under controlled conditions and preferrably includes a detergent in quantities sufficient to enhance the enzyme activity without adverse effects on the desirable substance (e.g. without adversely affecting the substances biological activity). The conditions are sufficient to assure degradation of the nucleic acids to a size or charge range that can be exploited in a subsequent separation or purification of the desired substance (such as a biologically active therapeutic substance). The process is especially useful in cases where the initial sizes and charges of the undesirable substance are similar (e.g. within ±50%) to those of the desirable substance to be purified. In these cases, the known specificity of a given enzyme system is then used to selectively change or degrade the undesirable substance in a manner that results in significant differences (e.g. reduction in average molecular size or charge of at least 50%) that can be exploited in one or more subsequent separation steps. Our process is illustrated in the examples below.

BRIEF DESCRIPTION OF THE FIGURE

FIG. 1 compares the reduction in DNA through precipitation and size exclusion chromatography with and without DNAse pre-treatment.

FIG. 2 compares the reduction in DNA through precipitation and ion exchange chromatography with and without DNAse pre-treatment.

FIG. 3 compares the reduction in DNA through precipitation, ion exchange and size exclusion chromatography with and without DNAse pre-treatment.

FIG. 4 compares the reduction in DNA through precipitation, ion exchange and size exclusion chromatography with and without DNAse.

SPECIFIC EMBODIMENTS

For purposes of discussion, the following definitions are presumed. Molecular size is considered equivalent to molecular weight (MW) as used in general practice. The molecular weight and configuration determine the molecular size. Size exclusion chromatography (SEC) is considered equivalent to rigorous gel filtration. Charge and charge density are considered equivalent in the applications to ion exchange chromatography (IEC).

Our process is illustrated using DNA-ases having a molecular weight ranging from 30,000 to 35,000 in either free form (in solution) or, preferably, in immobilized form to facilitate removal of the enzyme from the product and reduce enzyme consumption. Immobilization may be accomplished by techniques well known to those skilled in the art. DNA-ases I and II are used. DNA-ase I is an endonuclease cleaving 5' phosphodiester bands. DNA-ase II is an endonuclease cleaving 3' phosphodiester bands.

Various experiments were performed to demonstrate the digestion of DNA and subsequent removal. Parameters of time, temperature, pH, ionic species, and concentrations of components were studied. Data were generated to define conditions of optimal activity. The first experiments define kinetics of isolated DNA degradation upon exposure to types of DNAse (I, II; free, immobilized). Subsequent experiments demonstrate removal of DNA in several tissue culture fluids.

Purified DNA was isolated by phenol extraction and fractionated on SEC (Pharmacia FPLC Superose 6, a carbohydrate matrix) to isolate high molecular weight DNA of approximately 1 million daltons. Degradation was monitored by SEC and SDS-PAGE (sodium dodecyl sulfate polyacrylamide gel electrophoresis). DNA in tissue culture fluid was assayed by diphenylamine, fluorescent dye Hoescht 33258 (*Anal. Biochem.* 147, 289; 1985), P32 labeled nick-translated DNA and DNA probe dot blot hybridization (*Molecular Cloning*, a *Laboratory Manual*, Cold Spring Harbor; 1982).

PRELIMINARY EXPERIMENTS WITH PURIFIED DNA:

DNA DEGRADATION BY FREE AND IMMOBILIZED DNASE.

(a) Free enzyme 5 ml. of purified DNA were solubilized in a buffer of 0.1 M MgS04, 0.15 M NaCl, pH 7.4 0.001 g DNAse I (bovine pancreas, Sigma D-4763, D-5025) and 0.0005 g. DNAse II (Sigma D-4138) were added. After 4 hrs. mixing, samples were assayed on SEC and showed the absence of a high molecular weight peak. A peak at approximately 30,000 daltons M.W. was found. DNAse I and II have M.W. of 30,000 and 32,000 daltons, respectively.

(b) Immobilized enzyme

DNAse I was immobilized on a agarose matrix (Bio-Rad Affigel 10, 5.6 mg/ 3 ml gel) by coupling in 0.1 M NaHC03, pH 8.0, 4 C. Passage of purified DNA showed a consistent molecular weight degradation with each pass through the DNAse I column.

A single peak at approximately 1 million daltons was degraded to a single peak at approximately 30,000 daltons M.W. with 14 column passes. The fragments and enzyme appear to have approximately the same molecular weight.

DNAse II was immobilized separately on the agarose matrix, also.

(c) The presence of a detergent was studied. Tween 80, a non-ionic detergent, was found to increase enzymatic activity. Tween 80 is a trademark for (2)(-Sorbitan mono-9-octadecenoate poly (oxy-1,2-ethanediyl) derivative. 0.5% Tween increases degradation by 50% compared with 0.1% Tween 80.

(d) Enzyme activity may be reduced by exposing the solution to pH less than 4 or temperatures greater than 60 C.

EXPERIMENTS WITH FILTERED TISSUE CULTURE (TC) FLUIDS

EXAMPLE 1

Degradation of DNA with free enzyme followed by precipitation

Tissue culture fluid containing a therapeutic monoclonal antibody of class M (molecular weight 800,000) specific to Pseudomonas aeruginosa was produced by a cell line designated as Genetic Systems.6F11-E4. The cell line is a human hybridoma transformed with Epstein-Barr virus, thereby producing human and virus DNA. The 6F11 Cell Line has been deposited with the A.T.C.C. and has Accession No. CRL 8562. Tissue culture media is a mixture of Hana Biologics complex media supplemented with human serum albumin and other proteins.

In batch experiments, TC fluid with 0.01 M MgS04, 0.15 NaCl, 0.1 M NaOAc, pH 7.4 was mixed with 0.02 mg/ml DNAse I. Samples were taken over time and precipitated with 10% PEG, pH 7. PEG precipitates show a declining level of DNA, resulting in 6ug DNA/mg IgM. The DNA is degraded such that it no longer precipitates (remains in solution as small molecular weight components). Controls purified through the same process without enzyme treatment contain DNA at approximately 100 ug/mg IgM.

TABLE I

| Time (hrs.) | DNA in Precipitate (ug DNA/mg protein) With Enzyme | Without Enzyme |
| --- | --- | --- |
| 0 | 77 | 100 |
| 4 | 18 | |
| 8 | 12 | |
| 24 | 6 | 100 |

The experiment was repeated with 0.1 mg/ml DNAse I with 0.01 M MgS04. Similar results were observed, but kinetics were faster.

EXAMPLE 2

Degradation of DNA with free enzyme followed by precipitation and size exclusion chromatography (SEC)

The experiments described in Example 1 were expanded further.

The TC fluid incubated for 24 hours with DNAse and precipitated (6 ug DNA/mg protein) was fractionated on SEC (FPLC-Superose 6, a carbohydrate matrix). DNA was undetectable in the product peaks (< 1 pg/mg product). Controls purified through the same process without enzyme treatment contain approximately 0.1–1 ug DNA/mg IgM in SEC peaks.

EXAMPLE 3

Degradation of DNA with free enzyme followed by precipitation and ion exchange chromatography (IEC)

The experiments described in Example 1 were expanded further.

The TC fluid incubated for 24 hours with DNAse and precipitated (6 ug DNA/mg protein) was fractionated on ion exchange chromatography. The resin was Pharmacia DEAE Sepharose in a buffer of 0.05 M Tris, 0.05 M NaCl, pH 8. Elution of product was in 0.05 M Tris, 0.18 M NaCl, pH 8.

DNA was undetectable in the product peaks. Controls purified through the same process without enzyme treatment contain approximately 0.01–0.1 ug DNA/mg IgM in IEC peaks.

EXAMPLE 4

Degradation of DNA with immobilized enzyme followed by precipitation

Tissue culture fluid containing a monoclonal antibody of class M was produced as described in Example 1. DNAse I was immobilized as described in preliminary experiments.

TC fluid with 0.01 M MgS04 was passed through the NDAse matrix column repeatedly and precipitated with 10% PEG. The precipitate contained 0.4 ug DNA/mg protein. Controls purified through the same process without enzyme treatment contain approximately 100 ug DNA/mg IgM.

EXAMPLE 5

Degradation of DNA with immobilized enzyme followed by precipitation and size exclusion chromatography (SEC)

The experiments in Example 4 were expanded further.

TC fluid passed through the DNAse column and precipitated was fractionated on SEC. DNA was undetectable in the product peaks. Controls purified through the same process without enzyme treatment contain approximately 0.1-1ug DNA/mg product in SEC peaks.

Given the above disclosure, it is thought that numerous variations of our process will occur to those skilled in the art. Accordingly, it is intended that the above examples should be construed as illustrative and that the scope of the disclosed invention should be limited only by the following claims.

We claim:

1. A method of enhancing the removal of nucleic acids from cell culture fluid containing a desirable, biologically active therapeutic substance to be purified and undesirable nucleic acids having an average molecular size similar to the molecular size of the therapeutic substance, the method comprising the steps of contacting the fluid with nuclease enzymes in the presence of a detergent under conditions sufficient to assure the degradation of the nucleic acids to a molecular size range significantly different from the molecular size of the desirable substance, and then subjecting the fluid to at least one separation step sufficient to remove nucleic acids from the fluid.

2. The method of claim 1 wherein the nucleic acid is a DNA and the enzyme is a DNA-ase capable of degrading the DNA to less than about 50% of its original average moleculear weight.

3. The method of claim 1 wherein the separation step of step (b) comprises the use of precipitation, ion exchange or size exclusion chromatography.

4. A method of removing DNA from a cell culture fluid containing a biologically active, therapeutic substance expressed by the cells, the method comprising the steps of
   (a) incubating the fluid in the presence of a DNA-ase and a detergent in quantities sufficient to enhance the DNA-ase activity under conditions sufficient to degrade at least some of the DNA in the fluid; and
   (b) subjecting the fluid to a separation step capable of removing at least some of the degradation products formed in step (a).

5. The method of claim 4 wherein the DNA-ase is immobilized.

6. The method of claim 4 wherein the DNA-ase is immobilized on a carbohydrate support material.

7. The method of claim 4 wherein the cell culture fluid includes a monoclonal antibody or recombinant DNA expression product.

8. The method of claim 4 wherein the DNA content is reduced at least 10,000 fold.

9. The method of claim 4 wherein the original molecular weight of the DNA is within 50% of the molecular weight of the substance expressed by the cells.

10. The method of claim 4, wherein the detergent is non-ionic.

11. The method of claim 10 wherein the detergent is a (Z)-Sorbitan mono-9-octadecenoate) poly (oxy-1,2-ethanediyl) derivative.

* * * * *